(12) United States Patent
Becklund et al.

(10) Patent No.: US 10,485,981 B2
(45) Date of Patent: Nov. 26, 2019

(54) FIXATION METHODS FOR LEADLESS CARDIAC DEVICES

(71) Applicant: CARDIAC PACEMAKERS, INC., St. Paul, MN (US)

(72) Inventors: Joel Becklund, Roseville, MN (US); Bryan J. Swackhamer, Shoreview, MN (US); Robert A. Jones, Lake Elmo, MN (US); Danielle Frankson, Dayton, MN (US); Matthew P. Jones, Shoreview, MN (US); Brian L. Schmidt, White Bear Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 14 days.

(21) Appl. No.: 15/852,529

(22) Filed: Dec. 22, 2017

(65) Prior Publication Data

US 2018/0178023 A1 Jun. 28, 2018

Related U.S. Application Data

(60) Provisional application No. 62/439,271, filed on Dec. 27, 2016.

(51) Int. Cl.
*A61N 1/05* (2006.01)
*A61N 1/375* (2006.01)
(Continued)

(52) U.S. Cl.
CPC ..... *A61N 1/37518* (2017.08); *A61M 25/0068* (2013.01); *A61M 25/0082* (2013.01);
(Continued)

(58) Field of Classification Search
CPC .......... A61M 25/0068; A61M 25/0082; A61N 1/0573; A61N 1/0587; A61N 1/368;
(Continued)

(56) References Cited

U.S. PATENT DOCUMENTS

| 4,301,815 A | 11/1981 | Doring |
| 5,807,399 A | 9/1998 | Laske et al. |

(Continued)

FOREIGN PATENT DOCUMENTS

| EP | 2818201 B1 | 7/2016 |
| EP | 2658599 B1 | 10/2016 |

(Continued)

*Primary Examiner* — George Manuel
(74) *Attorney, Agent, or Firm* — Seager, Tufte & Wickhem LLP

(57) ABSTRACT

An implantable leadless pacing device may comprise a power source and circuitry operatively coupled to the power source. The circuitry configured to pace a patient's heart and/or sense electrical activity of the patient's heart. A housing may at least partially enclose the circuitry. The pacing device may further include a first electrode secured relative to the housing and a fixation mechanism secured relative to the housing. The fixation mechanism may comprise a plurality of tines configured to move between an elongated delivery configuration and a curved deployed configuration. Each tine of the plurality of tines may include a radiopaque material.

20 Claims, 10 Drawing Sheets

(51) Int. Cl.
*A61M 25/00* (2006.01)
*A61N 1/372* (2006.01)
*A61N 1/368* (2006.01)

(52) U.S. Cl.
CPC ........ *A61N 1/37512* (2017.08); *A61N 1/0573* (2013.01); *A61N 1/0587* (2013.01); *A61N 1/368* (2013.01); *A61N 1/37217* (2013.01); *A61N 1/37288* (2013.01); *A61N 2001/058* (2013.01)

(58) Field of Classification Search
CPC ............ A61N 1/37217; A61N 1/37288; A61N 1/37512; A61N 1/37518; A61N 2001/058
See application file for complete search history.

(56) References Cited

U.S. PATENT DOCUMENTS

| | | |
|---|---|---|
| 5,908,381 A | 6/1999 | Aznoian et al. |
| 6,181,973 B1 | 1/2001 | Ceron et al. |
| 6,224,725 B1 | 5/2001 | Glocker |
| 6,395,017 B1 | 5/2002 | Dwyer et al. |
| 6,409,674 B1 | 6/2002 | Brockway et al. |
| 6,497,803 B2 | 12/2002 | Glocker et al. |
| 6,551,477 B2 | 4/2003 | Glocker et al. |
| 6,582,441 B1 | 6/2003 | He et al. |
| 6,638,268 B2 | 10/2003 | Niazi |
| 6,786,918 B1 | 9/2004 | Krivoruchko et al. |
| 7,248,913 B2 | 7/2007 | Hassett |
| 7,321,798 B2 | 1/2008 | Muhlenberg et al. |
| 7,381,216 B2 | 6/2008 | Buzzard et al. |
| 7,499,758 B2 | 3/2009 | Cates et al. |
| 7,509,169 B2 | 3/2009 | Eigler et al. |
| 7,608,099 B2 | 10/2009 | Johnson et al. |
| 7,666,203 B2 | 2/2010 | Chanduszko et al. |
| 7,678,081 B2 | 3/2010 | Whiting et al. |
| 7,799,037 B1 | 9/2010 | He et al. |
| 7,840,281 B2 | 11/2010 | Kveen et al. |
| 7,937,161 B2 | 5/2011 | Hastings et al. |
| 7,993,351 B2 | 8/2011 | Worley et al. |
| 8,002,822 B2 | 8/2011 | Glocker et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bomzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,894,824 B2 | 11/2014 | Glocker et al. |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,272,155 B2 | 3/2016 | Ostroff |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,351,648 B2 | 5/2016 | Mothilal et al. |
| 9,358,387 B2 | 6/2016 | Suwito et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bomzin et al. |
| 9,468,773 B1 | 10/2016 | Anderson et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,675,798 B2 | 6/2017 | Grubac et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 2003/0078618 A1 | 4/2003 | Fey et al. |
| 2005/0021046 A1* | 1/2005 | Bilge ................ A61M 25/0068 606/108 |
| 2005/0101984 A1 | 5/2005 | Chanduszko et al. |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2006/0085041 A1* | 4/2006 | Hastings .............. A61N 1/0587 607/33 |
| 2009/0082828 A1 | 3/2009 | Ostroff |
| 2010/0274227 A1 | 10/2010 | Khairkhahan et al. |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0095539 A1 | 4/2012 | Khairkhahan et al. |
| 2012/0109148 A1 | 5/2012 | Bonner et al. |
| 2012/0172690 A1* | 7/2012 | Anderson ............ A61N 1/0573 600/347 |
| 2012/0172891 A1 | 7/2012 | Lee |
| 2012/0172892 A1 | 7/2012 | Grubac et al. |
| 2013/0012925 A1 | 1/2013 | Berthiaume et al. |
| 2013/0035636 A1 | 2/2013 | Beasley et al. |
| 2013/0096658 A1* | 4/2013 | Shan ..................... A61N 1/056 607/116 |
| 2013/0103047 A1 | 4/2013 | Steingisser et al. |
| 2013/0253342 A1 | 9/2013 | Griswold et al. |
| 2013/0253346 A1 | 9/2013 | Griswold et al. |
| 2014/0018818 A1 | 1/2014 | Somogyi et al. |
| 2014/0324145 A1 | 10/2014 | Eggen et al. |
| 2014/0378991 A1 | 12/2014 | Ollivier |
| 2015/0039070 A1 | 2/2015 | Kuhn et al. |

(56) References Cited

U.S. PATENT DOCUMENTS

| | | |
|---|---|---|
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114157 A1 | 4/2016 | Haasl et al. |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |

FOREIGN PATENT DOCUMENTS

| | | |
|---|---|---|
| EP | 2651502 B1 | 11/2016 |
| EP | 2771064 B1 | 1/2017 |
| EP | 2780077 B1 | 1/2017 |

* cited by examiner

FIXATION METHODS FOR LEADLESS CARDIAC DEVICES

CROSS REFERENCE TO RELATED APPLICATIONS

The present application claims the benefit of and priority to U.S. Provisional Patent Application Ser. No. 62/439,271, filed Dec. 27, 2016, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, an implantable leadless pacing device may comprise a power source, circuitry operatively coupled to the power source, the circuitry configured to pace a patient's heart and/or sense electrical activity of the patient's heart, a housing at least partially enclosing the circuitry, a first electrode secured relative to the housing and exposed to the environment outside of the housing, and a fixation mechanism secured relative to the housing, the fixation mechanism comprising a plurality of tines configured to move between an elongated delivery configuration and a curved deployed configuration. Each tine of the plurality of tines may include a radiopaque material.

Alternatively or additionally to any of the examples above, in another example, the radiopaque material may be a radiopaque coating.

Alternatively or additionally to any of the examples above, in another example, the radiopaque material may have a thickness of about 25 micrometers.

Alternatively or additionally to any of the examples above, in another example, the radiopaque coating may be deposited using physical vapor deposition.

Alternatively or additionally to any of the examples above, in another example, the radiopaque material may be a continuous coating substantially covering at least one surface of each tine of the plurality of tines.

Alternatively or additionally to any of the examples above, in another example, the radiopaque material may be a plurality of radiopaque bands positioned at intervals along a length of each tine of the plurality of tines.

Alternatively or additionally to any of the examples above, in another example, the plurality of tines may each comprise a nitinol tube having a lumen filled with the radiopaque material.

Alternatively or additionally to any of the examples above, in another example, the plurality of tines may be formed from a layered tube.

Alternatively or additionally to any of the examples above, in another example, the layered tube may be a rolled layered sheet.

Alternatively or additionally to any of the examples above, in another example, the layered tube may comprise an inner nitinol layer, an intermediate layer including the radiopaque material, and an outer nitinol layer.

Alternatively or additionally to any of the examples above, in another example, the layered tube may comprise an inner layer including the radiopaque material, an intermediate nitinol layer, and an outer layer including the radiopaque material Alternatively or additionally to any of the examples above, in another example, the radiopaque material comprises gold (Au), palladium (Pd), platinum (Pt), iridium (Ir), tantalum (Ta), osmium (Os), rhenium (Re), tungsten (W), niobium (Nb), and/or alloys containing at least one radiopaque material.

Alternatively or additionally to any of the examples above, in another example, the radiopaque material may comprise a radiopaque loaded polymer.

Alternatively or additionally to any of the examples above, in another example, the implantable leadless pacing device may further comprise an external coating disposed over the radiopaque material.

Alternatively or additionally to any of the examples above, in another example, the plurality of tines may each comprise a tubular member including the radiopaque material and having a lumen filled with nitinol.

In another example, an implantable leadless pacing device may comprise a power source, circuitry operatively coupled to the power source, the circuitry configured to pace a patient's heart and/or sense electrical activity of the patient's heart, a housing at least partially enclosing the circuitry, a first electrode secured relative to the housing and exposed to the environment outside of the housing, and a fixation mechanism secured relative to the housing. The fixation mechanism may comprise one or more nitinol tines configured to move between an elongated delivery configuration and a curved deployed configuration and a radiopaque coating disposed on a surface of at least one tine of the one or more nitinol tines.

Alternatively or additionally to any of the examples above, in another example, the radiopaque coating may have a thickness in the range of 5 to 100 micrometers.

Alternatively or additionally to any of the examples above, in another example, the radiopaque coating may be deposited using physical vapor deposition.

Alternatively or additionally to any of the examples above, in another example, the radiopaque coating may be a continuous coating substantially covering at least one surface of each tine of the one or more tines.

Alternatively or additionally to any of the examples above, in another example, the radiopaque coating may be a plurality of radiopaque bands positioned at intervals along a length of each tine of the one or more tines.

Alternatively or additionally to any of the examples above, in another example, the radiopaque coating may comprise gold (Au), palladium (Pd), platinum (Pt), iridium (Ir), tantalum (Ta), osmium (Os), rhenium (Re), tungsten (W), niobium (Nb), and/or alloys containing at least one radiopaque material.

Alternatively or additionally to any of the examples above, in another example, the radiopaque coating comprises a radiopaque loaded polymer.

Alternatively or additionally to any of the examples above, in another example, the implantable leadless pacing device may further comprising an external coating disposed over the radiopaque coating.

Alternatively or additionally to any of the examples above, in another example, the external coating may comprise parylene.

In another example, an implantable leadless pacing device may comprise a power source, circuitry operatively coupled to the power source, the circuitry configured to pace a patient's heart and/or sense electrical activity of the patient's heart, a housing at least partially enclosing the circuitry, a first electrode secured relative to the housing and exposed to the environment outside of the housing and a fixation mechanism secured relative to the housing. The fixation mechanism may comprise a plurality of tines configured to move between an elongated delivery configuration and a curved deployed configuration. Each tine of the plurality of tines may include a radiopaque material.

Alternatively or additionally to any of the examples above, in another example, the plurality of tines may each comprise a nitinol tube having a lumen filled with the radiopaque material.

Alternatively or additionally to any of the examples above, in another example, the plurality of tines may each comprise a tubular member including the radiopaque material and having a lumen filled with nitinol.

Alternatively or additionally to any of the examples above, in another example, the plurality of tines may be formed from a layered tube.

Alternatively or additionally to any of the examples above, in another example, the layered tube may be a rolled layered sheet.

Alternatively or additionally to any of the examples above, in another example, the layered tube may comprise an inner nitinol layer, an intermediate layer including the radiopaque material, and an outer nitinol layer.

Alternatively or additionally to any of the examples above, in another example, the radiopaque material may comprise gold (Au), palladium (Pd), platinum (Pt), iridium (Ir), tantalum (Ta), osmium (Os), rhenium (Re), tungsten (W), niobium (Nb), and/or alloys containing at least one radiopaque material.

Alternatively or additionally to any of the examples above, in another example, the radiopaque material may comprise a radiopaque loaded polymer.

In another example, a fixation mechanism for securing an implantable leadless pacing device to a tissue may comprise a plurality of tines configured to move between an elongated delivery configuration and a curved deployed configuration. Each tine of the plurality of tines may include a radiopaque material.

Alternatively or additionally to any of the examples above, in another example, the radiopaque material may comprises gold (Au), palladium (Pd), platinum (Pt), iridium (Ir), tantalum (Ta), osmium (Os), rhenium (Re), tungsten (W), niobium (Nb), and/or alloys containing at least one radiopaque material.

Alternatively or additionally to any of the examples above, in another example, the radiopaque material may comprise a radiopaque loaded polymer.

The above summary of some embodiments is not intended to describe each disclosed embodiment or every implementation of the present disclosure. The FIGS., and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
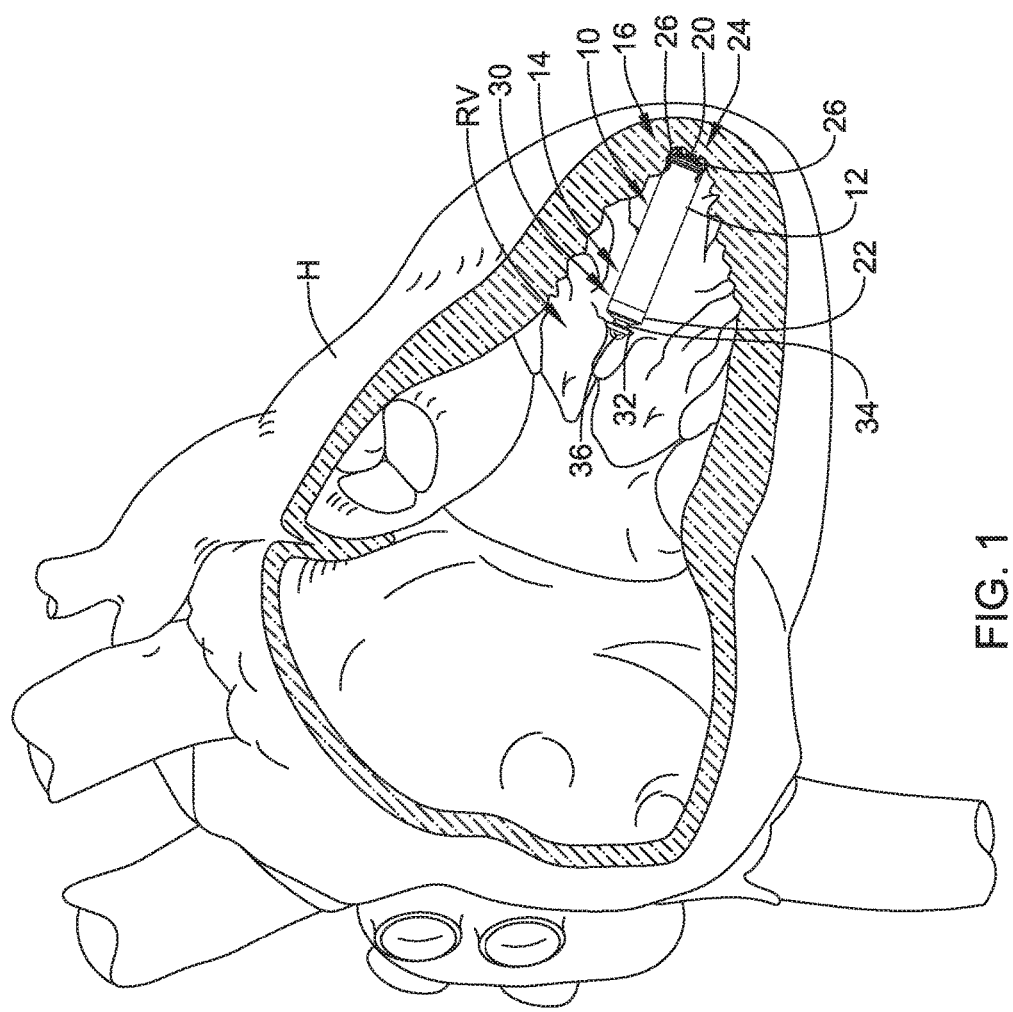
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature as well as mechanisms to confirm fixation of the capsule.

Figure 2:
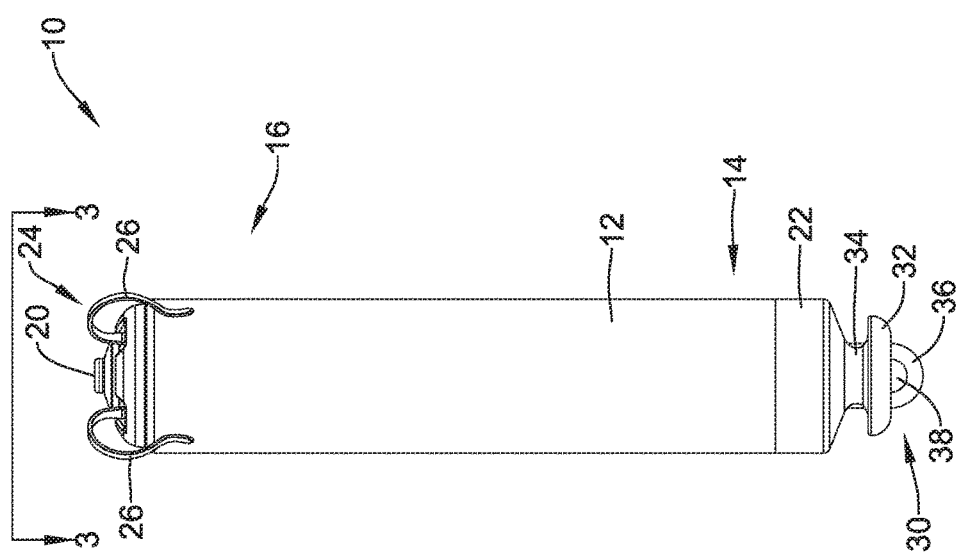
FIG. 2 is a side view of an example implantable leadless cardiac pacing device.
Figure 3:
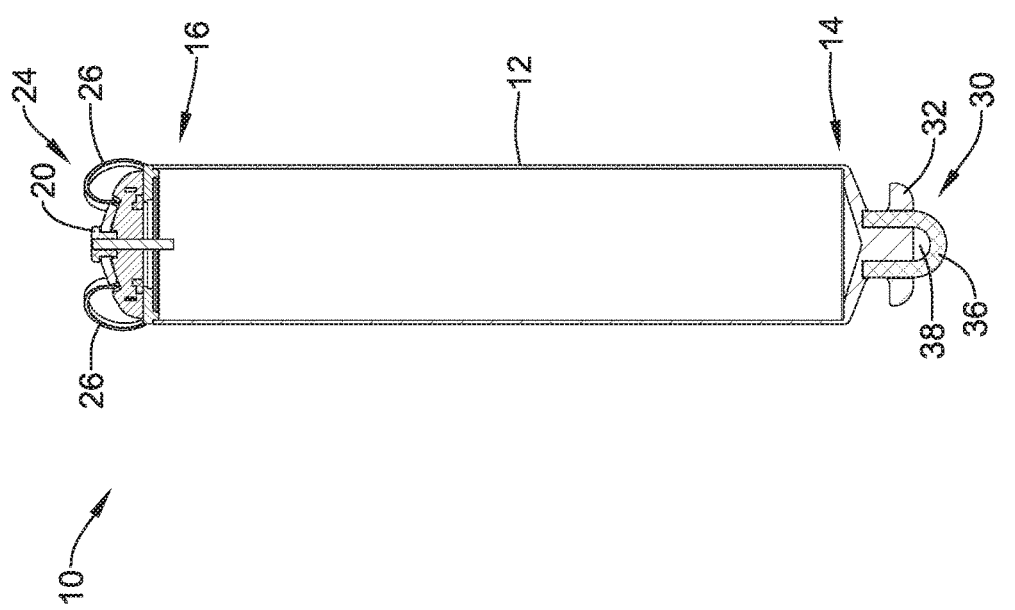
FIG. 3 is a cross-sectional view of the implantable leadless cardiac pacing device of FIG. 2.

FIG. 1 illustrates an example implantable leadless cardiac pacing device 10 (e.g., a leadless pacemaker) implanted in a chamber of a heart H, such as the right ventricle RV. A side view of the illustrative implantable device 10 is shown in FIG. 2 and a cross-sectional view of the illustrative implantable device 10, taken at line 3-3 in FIG. 2, is illustrated in FIG. 3. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue. However, in some cases, the second electrode 22 may be spaced from the first electrode 20, but also in contact with the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks or tines 26 anchored into the cardiac tissue of the heart H to attach the implantable device 10 to a tissue wall. In other instances, the fixation mechanism 24 may include one or more, or a plurality of active or passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g., looped) through the opening 38. The retention structure 36 may extend though the head portion 32, along the neck portion 34, and to or into the proximal end 14 of the housing 12, as is shown more clearly in FIG. 3. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the visibility of the fixation mechanism 24. The fixation mechanism 24 may be formed from nitinol or other shape memory material which allows the tines 26 to be biased into a straightened configuration for advancing the device 10 to the implant location. The tines 26 may be maintained in the straightened configuration during advancement using, for example, a sheath and allowed to assume the curved shape shown in FIGS. 2 and 3 when the device 10 is in the desired location. In other words, the tines 26 may be advanced into the heart tissue in a straight configuration and when implant location is confirmed, the sheath or biasing force removed to allow the tines 26 to bend and attach the implantable device 10 to the tissue wall. During implantation of the implantable device 10, the hooks or tines 26 of the fixation mechanism may be difficult to observe using fluoroscopy.

Visibility of the implantable device 10 may be a function of, but is not limited to, fluoroscopy equipment and settings, viewing angle, patient anatomy, the geometry of the device 10 and/or the materials of the device 10. It is contemplated that making the fixation mechanism 24 more visible under fluoroscopy may help to provide a physical indication of fixation during the implantation procedure. In some instances, a radiopaque material such as, but not limited to gold (Au), palladium (Pd), platinum (Pt), iridium (Ir), tantalum (Ta), osmium (Os), rhenium (Re), tungsten (W), niobium (Nb), alloys containing at least one radiopaque material, and/or combinations thereof, may be used to increase the radiopacity of the fixation mechanism 24. Improving the visibility of the fixation mechanism 24 may allow the physician to observe a physical indication (e.g. using fluoroscopy) of the fixation mechanism 24 upon application of strain (e.g. a tugging or pulling force applied to the implantable device 10 prior to removal of the delivery system).

Figure 4:
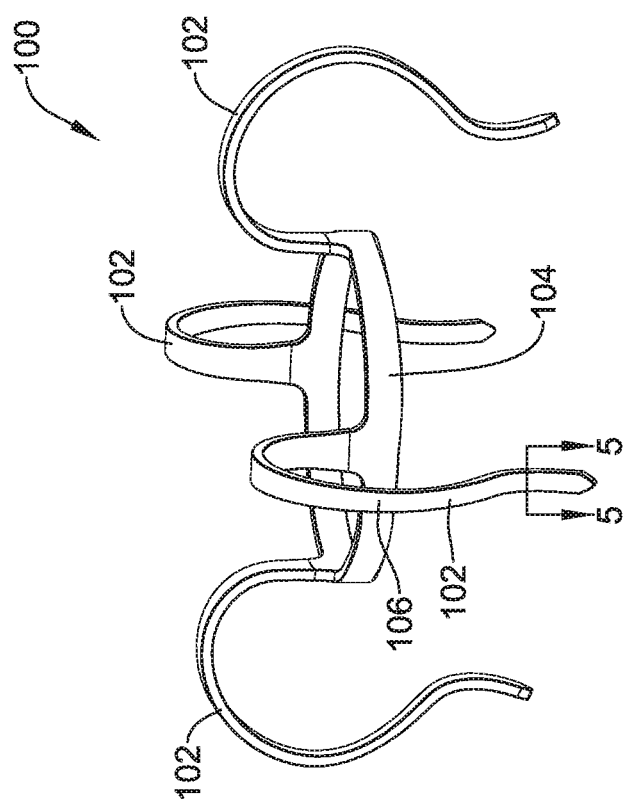
FIG. 4 is a perspective view of an illustrative fixation mechanism for use with an implantable leadless cardiac pacing device.

FIG. 4 is a perspective view of an illustrative fixation mechanism 100 for use with an implantable leadless cardiac pacemaker such as the implantable device 10 described herein. The fixation mechanism 100 may include one or more hooks or tines 102 configured to anchor to the cardiac tissue of the heart. While the fixation mechanism 100 is illustrated as including four tines 102, it is contemplated that the fixation mechanism 100 may include any number of tines 102 such as but not limited to, one, two, three, four, or more. The tines 102 may be interconnected through a ring 104 configured to secure the fixation mechanism 100 to a leadless cardiac pacemaker. It is contemplated that the fixation mechanism 100 may take other forms, including but not limited to one or more, or a plurality of active or passive tines, configured to entangle with trabeculae within the chamber of the heart and/or a helical fixation anchor configured to be screwed into a tissue wall to anchor the implantable device 10 to the heart.

In some cases, the fixation mechanism 100 may include a radiopaque coating 106 disposed over all (e.g., the entire surface area) or a portion of the tines 102 and/or ring 104. In some cases, the radiopaque coating 106 may include, but is not limited to gold (Au), palladium (Pd), platinum (Pt), iridium (Ir), tantalum (Ta), osmium (Os), rhenium (Re), tungsten (W), niobium (Nb), alloys containing at least one radiopaque material, and/or combinations thereof, to increase the radiopacity of the fixation mechanism 100.

Figure 5:
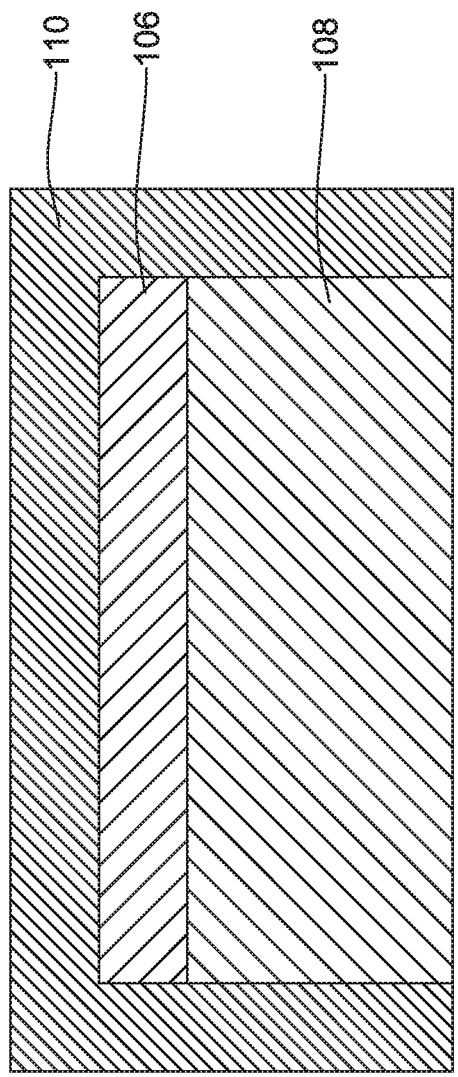
FIG. 5 is a cross-sectional view of a portion of the fixation mechanism of FIG. 4.

FIG. 5 is a cross-sectional view of the body of a tine 102, taken at line 5-5 of FIG. 4. The radiopaque coating 106 may be disposed over a base material 108, such as, but not limited to nitinol, which allows the tines 102 to move between an elongated or straightened delivery configuration (not explicitly shown) and a bent or curved fixation configuration as shown in FIG. 4. While FIG. 5 illustrates the radiopaque coating 106 on a single surface or side of the base material 108, it should be understood that the radiopaque coating 106 may be disposed over all of the surfaces (e.g., fully encompass or surround) of the base material 108 or any fraction of the surfaces desired. In some cases, the radiopaque coating 106 may be a continuous coating substantially covering at least one surface of each of the tines 102. However, the radiopaque coating 106 need not extend fully across the entire distance of a side of the base material 108. In some cases, the radiopaque coating 106 may be disposed on two or three sides of the base material 108. While the base material 108 is illustrated as having a generally rectangular cross-section, portions of the fixation mechanism 100 are not intended to be limited to any particular cross-sectional shape. For example, the cross-sectional shape of the tines 102, ring 104, or any other structure of the fixation mechanism 100 may be circular, oblong, square, triangular, polygonal, eccentric, etc., as desired.

In some embodiments, the radiopaque coating 106 may be applied to the surfaces (e.g., to the base material 108) of the fixation mechanism 100 using physical vapor deposition coating techniques including but not limited to sputter coating, multi-arc ion plating, etc. In some instances, a radiopaque coating 106 thickness of in the range of 5 micrometers (µm) may be a lower boundary of where the fixation mechanism 100 starts to become readily visible under fluoroscopy. Increasing the thickness of the radiopaque coating 106 may increase the visibility of the fixation mechanism 100. For example, a radiopaque coating 106 having a thickness of in the range of 25 µm may be more visible than a thickness in the range of 17 µm which may be more visible than a thickness in the range of 8 µm. It is contemplated that the radiopaque coating 106 may have a thickness in the range of 5 µm to 100 µm, 10 µm to 40 µm, or about 25 µm. However, the radiopaque coating 106 may have any thickness desired including thicknesses of less than 5 µm or greater than 50 µm.

In some embodiments, the radiopaque coating 106 may be a radiopaque loaded polymer. For example, a polymeric material such as, but not limited to polydimethylsiloxane (PDMS), polyether block amide (PEBAX), polyether urethane (PEUR), etc., may be loaded with a radiopaque material. The radiopaque material may include, but is not limited to, barium sulfate ($BaSO_4$), Au, Pd, Pt, Ir, Ta, Os, Re, W, or Nb powder, or powdered alloys containing at least one radiopaque metal, and oxide and/or carbide powders of any of the aforementioned metals (including, but not limited to tungsten carbide, bismuth subcarbonate, etc.). In some instances, the radiopaque coating 106 may be overmolded onto the base material 108. It is contemplated that the thickness of the radiopaque coating 106 formed from a radiopaque loaded polymer may be in the range of 5 µm to 50 µm, 10 µm to 40 µm, or about 25 µm. However, the radiopaque coating 106 may have any thickness desired including thicknesses of less than 5 µm or greater than 50 µm.

Due to the nature of the usage of the fixation mechanism 100 (e.g., deformation during delivery and flexing with movement of the heart after implantation), the materials selected should withstand high strains during delivery in addition to the high cycles of lower strain throughout device life. In some cases, radiopaque materials may not have the same super-elastic properties as nitinol. It may be desirable to avoid stress concentrations and reduce material internal stresses in the radiopaque coating 106. In some instances, this may be achieved through the use of a discontinuous radiopaque coating 106.

In some cases, a protective coating or external layer 110 may be applied over the radiopaque coating 106 for corrosion protection. For example, some radiopaque materials including, but not limited to Au, Pd, Pt, Ir, Ta, Os, Re, may not be galvanically compatible with the nitinol base material 108. The coating 110 may provide a permanent or semi-permanent isolation layer to reduce or eliminate galvanic corrosion risk. It is contemplated that the external layer 110 may hermetically isolate any areas where the two materials (e.g., the base material 108 and the radiopaque coating 106) would otherwise be exposed to the external environment. However, the external layer 110 may be disposed over any portion of the radiopaque coating 106 and/or base material 108 desired. For example, in some cases the external layer 110 may completely surround the outer surfaces of the radiopaque coating 106 and the base material 108. In other embodiments, the external layer 110 may be disposed over only a portion of the outer surfaces of the radiopaque coating 106 and/or base material 108, as desired. The external coating 110 may be any material that reduces or eliminates galvanic action between the radiopaque coating 106 and base material 108 by preventing contact with blood or other bodily fluid or tissue. Some illustrative materials for the external coating may include, but are not limited to parylene, silicone, titanium, a hydrophobic material, etc.

Figure 6:
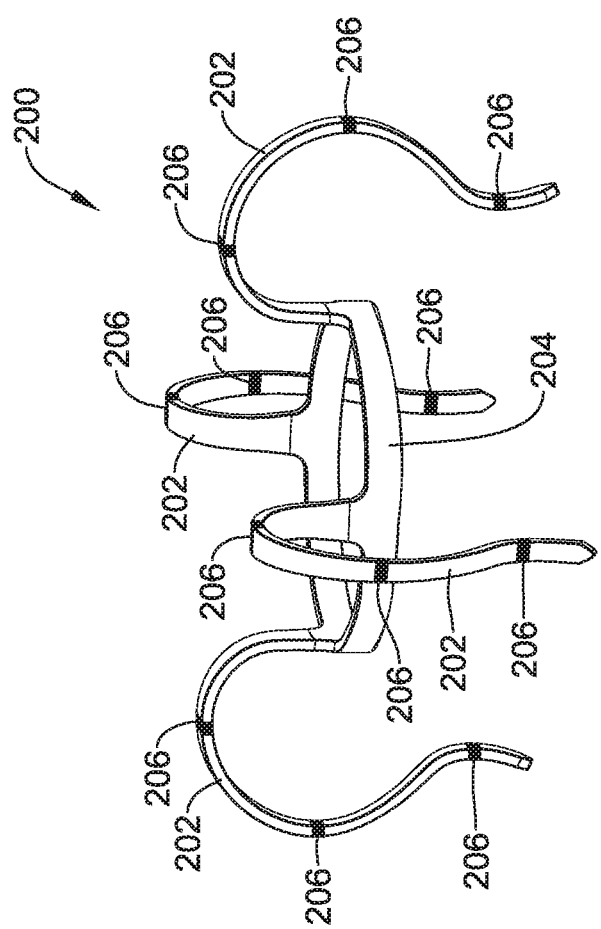
FIG. 6 is a side view of another illustrative fixation mechanism for use with an implantable leadless cardiac pacing device.

FIG. 6 is a side view of another illustrative fixation mechanism 200 for use with an implantable leadless cardiac pacemaker such as the implantable device 10 described herein. The fixation mechanism 200 may include one or more hooks or tines 202 configured to anchor to the cardiac tissue of the heart. The fixation mechanism 200 may be similar in form and function to the fixation mechanism 100 described above. The tines 202 may be interconnected through a ring 204 configured to secure the fixation mechanism 200 to a leadless cardiac pacemaker. It is contemplated that the fixation mechanism 200 may take other forms, including but not limited to one or more, or a plurality of active or passive tines, configured to entangle with trabeculae within the chamber of the heart and/or a helical fixation anchor configured to be screwed into a tissue wall to anchor the implantable device to the heart.

In some cases, the fixation mechanism 200 may include a plurality of radiopaque bands or dots 206. In some cases, the radiopaque bands 206 may be formed from, but are not limited to gold (Au), palladium (Pd), platinum (Pt), iridium (Ir), tantalum (Ta), osmium (Os), rhenium (Re), tungsten (W), niobium (Nb), alloys containing at least one radiopaque material, and/or combinations thereof, to increase the radiopacity of the fixation mechanism 200. In other cases the radiopaque bands 206 may be formed from a radiopaque loaded polymer such as any of those described herein. While not explicitly shown, the fixation mechanism 200 may include a protective or external coating similar in form and function to the external coating 110 described above to protect the fixation mechanism 200 from corrosion and/or galvanic action.

It is contemplated that the radiopaque bands 206 may be positioned on the tines 202 at discrete intervals along a length of the tines 202. In some cases, each tine 202 may include radiopaque bands 206 while in other cases, only some of the tines 202 may include radiopaque bands 206. Each tine 202 may include, zero, one, two, three, four, or more radiopaque bands 206. In some embodiments, the radiopaque bands 206 may be positioned at evenly spaced intervals. In other embodiments, the radiopaque bands 206 may be positioned at non-uniformly spaced intervals, as desired. In the example shown in FIG. 6, the radiopaque bands 206 are positioned at the bends in the tines 202. For example, the radiopaque bands 206 may be positioned at inflection points of the tines 202 where the curvature of the tines 202 changes. However, this is not required. The radiopaque bands 206 may be positioned at any location desired. In some embodiments, the radiopaque bands 206 may extend around an entire perimeter of the tine 202. In other embodiments, the radiopaque bands 206 may be positioned on less than an entire outer perimeter of the tine 202.

The radiopaque bands 206 may form a "constellation", pattern, or shape of radiopaque components. The constellation or pattern of the radiopaque bands 206 may change shape or configuration under an applied strain. For example, once the fixation mechanism 200 has been deployed into the heart wall, the physician may exert a pulling force on the implantable device 10 to verify the fixation mechanism 200 has been engaged with the heart wall. If the fixation mechanism 200 has be secured to the heart wall, the tines 202 may bend or flex (e.g., temporarily change shape) under the pulling force of the physician resulting in a temporary change in the shape of the constellation or pattern of the radiopaque bands 206. This may allow a physician to visually confirm adequate fixation of the implantable device 10 under fluoroscopy. Conversely, the tines 202 of a fixation mechanism 200 that is not secured or not well secured may not bend or flex (e.g., temporarily change shape) under the pulling force of the physician. As such, no change or very little change in the constellation or pattern of the radiopaque bands 206 may be observed, indicating that the implantable device 10 has not been adequately secured.

The radiopaque bands 206 may be secured to or disposed on the tines 202 or other portion of the fixation mechanism 200 using any number of methods. In a first example, the radiopaque bands 206 may be created via physical vapor deposition coating techniques including but not limited to sputter coating, multi-arc ion plating, etc. In another example, the radiopaque bands 206 may be press-fit, swaged, riveted, molded, adhered, welded, or otherwise mechanically coupled to the tines 202. It is contemplated that the when using coating, dipping, or molding techniques the tines 202 may need to be masked prior to applying the radiopaque bands 206 to prevent the radiopaque material from covering the entire tine 202.

Figure 7:
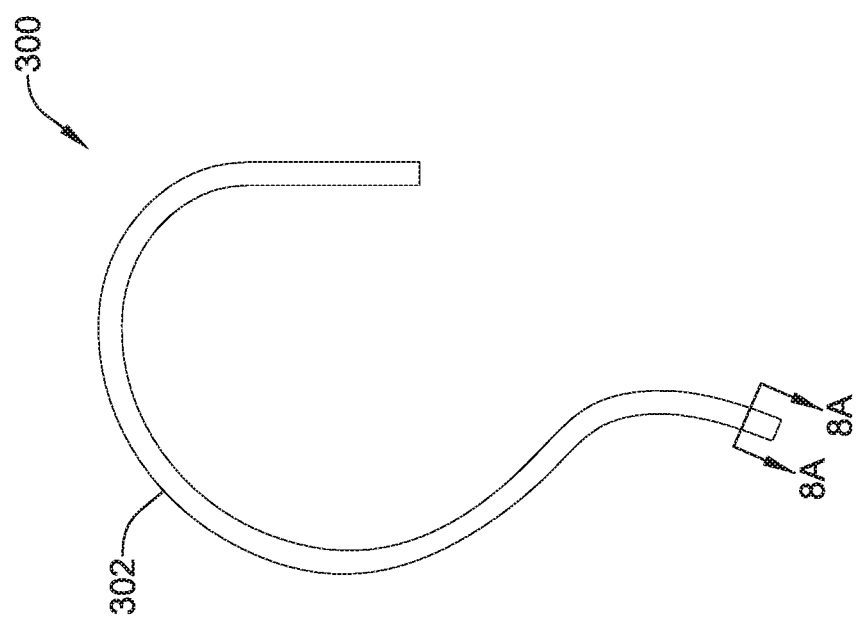
FIG. 7 is a side view of another illustrative fixation element for use with an implantable leadless cardiac pacing device.

FIG. 7 is a perspective view of another illustrative fixation element 300 for use with an implantable leadless cardiac pacemaker such as the implantable device 10 described herein. The fixation element 300 may be a drawn-filled tube 302 which may be shaped into a curved hook or tine. One or more of these fixation elements 300 may be individually attached or coupled to an implantable device 10 to form a fixation mechanism. It is contemplated that the fixation element 300 may take other shapes as desired, including, but not limited to passive times or a helical fixation anchor. The fixation element(s) 300 may be configured to anchor to the cardiac tissue of the heart. Any number of fixation elements 300 may be used to form a fixation mechanism such as one, two, three, four, or more.

Figure 8A:
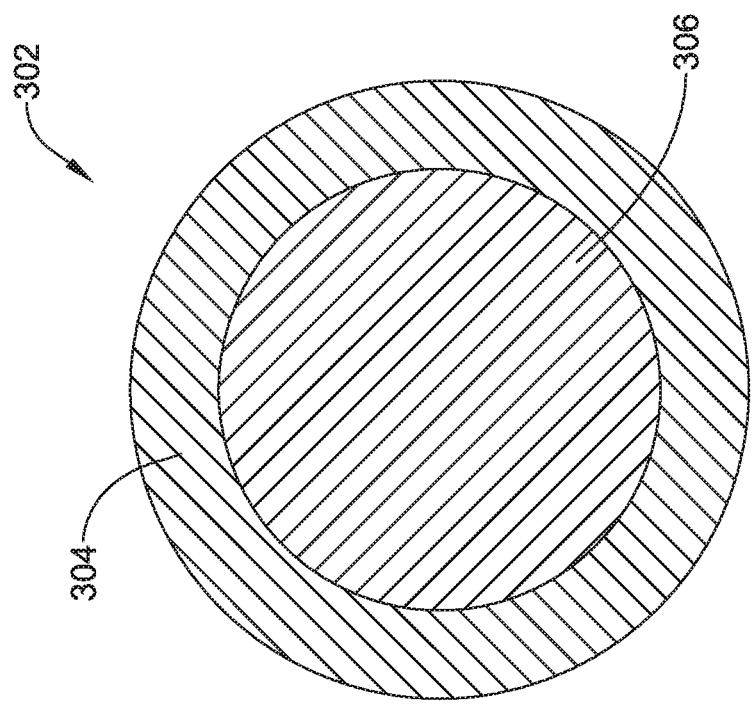
FIG. 8A is a cross-sectional view of the fixation element of FIG. 7.

FIG. 8A is a cross-sectional view of the fixation element 300 formed with a drawn-filled tube, taken at line 8A-8A of FIG. 7. The fixation element 300 may include an outer tubular member 304 and an inner core 306. The outer tubular member 304 may be may be nitinol, or other material which allows the fixation element 300 to move between an elongated or straightened delivery configuration (not explicitly shown) and a bent or curved fixation configuration as shown in FIG. 7. The reverse configuration is also contemplated in which the inner core 306 is nitinol, or other material which allows the fixation element 300 to move between an elongated or straightened delivery configuration (not explicitly shown) and a bent or curved fixation configuration as shown in FIG. 7 The drawn-filled tube 302 may be formed by drawing the outer tubular member 304 and inner core 306.

Figure 8B:
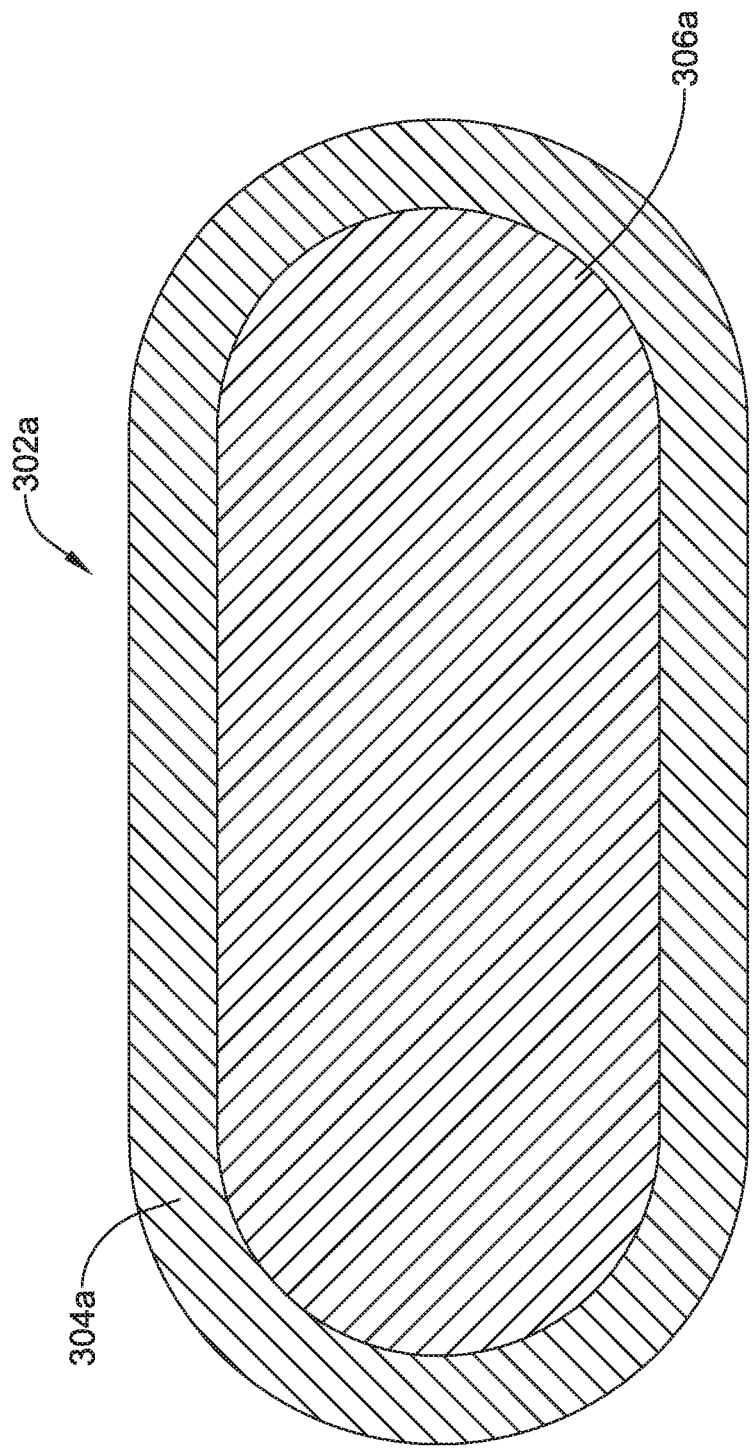
FIG. 8B is an alternative cross-sectional view of the fixation element of FIG. 7.

In some embodiments, the inner core material 306 and/or outer tubular member 304 may be a radiopaque material. The radiopaque material may include, but is not limited to gold (Au), palladium (Pd), platinum (Pt), iridium (Ir), tantalum (Ta), osmium (Os), rhenium (Re), tungsten (W), niobium (Nb), alloys containing at least one radiopaque material, and/or combinations thereof, to increase the radiopacity of the fixation element 300. In some embodiments, the drawn-filled tube 302 may be mechanically deformed to form a less-round or non-circular cross-sectional shape. It is contemplated that the mechanical deformation may occur before or after filling the outer tubular member 304, as desired. FIG. 8B is a cross-sectional view of a drawn-filled tube 302*a* which has been mechanically deformed such that the outer tubular member 304*a* and the inner core 306*a* have an oblong shape. This is just an example. Other non-circular shapes may be used, as desired. While not explicitly shown, the fixation element 300, 300*a* may include a protective or external coating similar in form and function to the external coating 110 described above to protect the fixation mechanism 300, 300*a* from corrosion and/or galvanic action.

Figure 9:
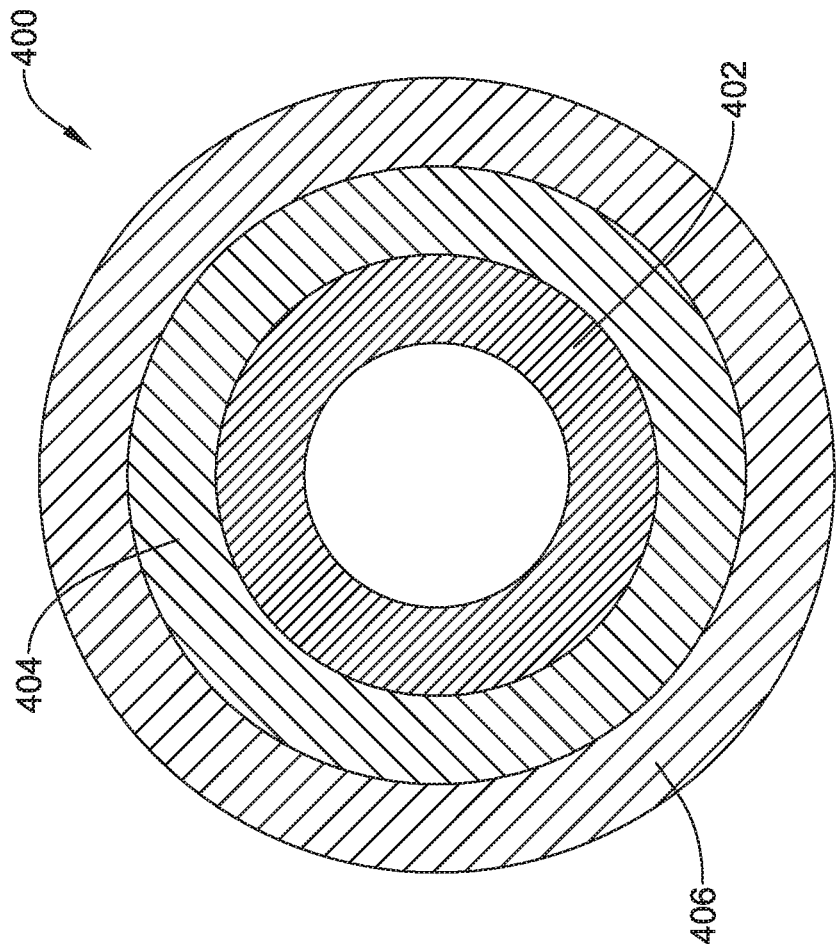
FIG. 9 is a cross-sectional view of a tubular member for forming an illustrative fixation mechanism.

FIG. 9 is a cross-sectional view of an illustrative tubing 400 that may be used to form a fixation mechanism for use with an implantable leadless cardiac pacemaker such as the implantable device 10 described herein. In some embodiments, the cross-section of the tubing 400 may be a continuous ring. In other words, the tubing 400 may not include seams or joints. In other embodiments, the tubing 400 may be formed by layered sheet which has been bent or curved to form a tube and secured at a seam thereof.

The tubing 400 may include an inner layer 402, an intermediate layer 404, and an outer layer 406. In some instances, the inner layer 402 and outer layer 406 may be formed from nitinol, or other material, which may allow a fixation mechanism to be temporarily deformed. The intermediate layer 404 may be a radiopaque material. The inverse configuration is also contemplated in which one or both the inner layer 402 and/or outer layer 406 are formed from a radiopaque material and at least one of the inner layer 402, intermediate layer 404 and/or outer layer 406 are formed from nitinol, or other material, which may allow a fixation mechanism to be temporarily deformed. The radiopaque material may include, but is not limited to gold (Au), palladium (Pd), platinum (Pt), iridium (Ir), tantalum (Ta), osmium (Os), rhenium (Re), tungsten (W), niobium (Nb), alloys containing at least one radiopaque material, and/or combinations thereof, to increase the radiopacity of the tubing 400.

In some embodiments, the tubing 400 may be formed through a series of drawing and annealing steps to achieve the final tubing size. Once the final tubing size (e.g. a desired inner diameter, a desired outer diameter, and/or a desired thickness) has been obtained, laser cutting or electrical discharge machining (EDM) may be used to cut a fixation mechanism from the tubing 400. Once the general shape has been cut from the tubing 400, the fixation mechanism may be formed into a shape that is similar in structure to the fixation mechanism 100 illustrated in FIG. 4. It is contemplated that hard tooling and high temperatures may be used to form the nitinol structural shape and to anneal the intermediate layer 404. While not explicitly shown, the final fixation mechanism may include a protective or external coating similar in form and function to the external coating 110 described above to protect the fixation mechanism (e.g., the exposed radiopaque material at cut edges) from corrosion and/or galvanic action.

The materials that can be used for the various components of the implantable leadless cardiac pacemaker, such as the implantable device 10 (and/or other device structures including the various fixation mechanisms 24, 100, 200, 300 disclosed herein) and the various members disclosed herein may include those commonly associated with medical devices. For simplicity purposes, the following discussion makes reference the implantable device 10 and components of thereof. However, this is not intended to limit the devices and methods described herein, as the discussion may be applied to other similar delivery systems and/or components of delivery systems or devices disclosed herein.

The implantable device 10 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; platinum; iridium; palladium; tungsten; titanium; combinations thereof; and the like; or any other suitable material.

In at least some embodiments, portions or all of the implantable device 10 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the implantable device 10 in determining its location and orientation. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the implantable device 10 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable leadless pacing device comprising:
a power source;
circuitry operatively coupled to the power source, the circuitry configured to pace a patient's heart and/or sense electrical activity of the patient's heart;
a housing at least partially enclosing the circuitry;
a first electrode secured relative to the housing and exposed to the environment outside of the housing; and
a fixation mechanism secured relative to the housing, the fixation mechanism comprising:
one or more nitinol tines configured to move between an elongated delivery configuration and a curved deployed configuration; and
a radiopaque coating disposed on a surface of at least one tine of the one or more nitinol tines; and
wherein the radiopaque coating is a plurality of radiopaque bands positioned at intervals along a length of each tine of the one or more tines.

2. The implantable leadless pacing device of claim 1, wherein the radiopaque coating has a thickness in the range of 5 to 100 micrometers.

3. The implantable leadless pacing device of claim 1, wherein the radiopaque coating is deposited using physical vapor deposition.

4. The implantable leadless pacing device of claim 1, wherein the radiopaque coating comprises gold (Au), palladium (Pd), platinum (Pt), iridium (Ir), tantalum (Ta), osmium (Os), rhenium (Re), tungsten (W), niobium (Nb), and/or alloys containing at least one radiopaque material.

5. The implantable leadless pacing device of claim 1, wherein the radiopaque coating comprises a radiopaque loaded polymer.

6. The implantable leadless pacing device of claim 1, further comprising an external coating disposed over the radiopaque coating.

7. The implantable leadless pacing device of claim 6, wherein the external coating comprises parylene.

8. The implantable leadless pacing device of claim 1, wherein a first one of the plurality of radiopaque bands is positioned at a distalmost extent of each tine of the one or more tines when the one or more tines are in the curved deployed configuration, and a second one of the plurality of radiopaque bands is positioned at a radial outwardmost extent of each tine of the one or more tines when the one or more tines are in the curved deployed configuration.

9. An implantable leadless pacing device comprising:
a power source;
circuitry operatively coupled to the power source, the circuitry configured to pace a patient's heart and/or sense electrical activity of the patient's heart;
a housing at least partially enclosing the circuitry;
a first electrode secured relative to the housing and exposed to the environment outside of the housing; and
a fixation mechanism secured relative to the housing, the fixation mechanism comprising a plurality of tines configured to move between an elongated delivery configuration and a curved deployed configuration;
wherein each tine of the plurality of tines includes a radiopaque material; and
wherein at least some of the plurality of tines include a plurality of radiopaque bands positioned at intervals along a length of each tine, the plurality of bands positioned at one or more bends of the plurality of tines when the plurality of tines are in the curved deployed configuration.

10. The implantable leadless pacing device of claim 9, wherein at least some of the plurality of tines each comprise a nitinol tube having a lumen filled with the radiopaque material.

11. The implantable leadless pacing device of claim 10, wherein the radiopaque material comprises gold (Au), palladium (Pd), platinum (Pt), iridium (Ir), tantalum (Ta), osmium (Os), rhenium (Re), tungsten (W), niobium (Nb), and/or alloys containing at least one radiopaque material.

12. The implantable leadless pacing device of claim 10, wherein the radiopaque material comprises a radiopaque loaded polymer.

13. The implantable leadless pacing device of claim 9, wherein at least some of the plurality of tines each comprise a tubular member including the radiopaque material and having a lumen filled with nitinol.

14. The implantable leadless pacing device of claim 9, wherein at least some of the plurality of tines are formed from a layered tube.

15. The implantable leadless pacing device of claim 14, wherein at least some of the layered tube is a rolled layered sheet.

16. The leadless pacing device of claim 14, wherein the layered tube comprises an inner nitinol layer, an intermediate layer including the radiopaque material, and an outer nitinol layer.

17. The implantable leadless pacing device of claim 9, wherein at least one radiopaque band of the plurality of radiopaque bands is positioned at a radial outwardmost extent of at least one of the tines when the plurality of tines are in the curved deployed configuration.

18. A fixation mechanism for securing an implantable leadless pacing device to a tissue, the fixation mechanism comprising:
a plurality of tines configured to move between an elongated delivery configuration and a curved deployed configuration;
wherein each tine of the plurality of tines includes a first material, a radiopaque material disposed on a surface of the first material, and a coating extending over at least an entirety of the radiopaque material, the coating configured to inhibit galvanic action between the first material and the radiopaque material.

19. The fixation mechanism of claim 18, wherein the radiopaque material comprises gold (Au), palladium (Pd), platinum (Pt), iridium (Ir), tantalum (Ta), osmium (Os), rhenium (Re), tungsten (W), niobium (Nb), and/or alloys containing at least one radiopaque material.

20. The fixation mechanism of claim 18, wherein the radiopaque material comprises a radiopaque loaded polymer.

\* \* \* \* \*